(12) United States Patent
Palmer et al.

(10) Patent No.: US 6,544,231 B1
(45) Date of Patent: Apr. 8, 2003

(54) CATCH, STOP AND MARKER ASSEMBLY FOR A MEDICAL INSTRUMENT AND MEDICAL INSTRUMENT INCORPORATING THE SAME

(75) Inventors: Matthew A. Palmer, Miami, FL (US); Jose Luis Francese, Springs, FL (US)

(73) Assignee: Medcanica, Inc., Miami, FL (US)

( * ) Notice: Subject to any disclaimer, the term of this patent is extended or adjusted under 35 U.S.C. 154(b) by 0 days.

(21) Appl. No.: 09/575,432

(22) Filed: May 22, 2000

(51) Int. Cl.[7] .............................................. A61M 5/178
(52) U.S. Cl. ........................... 604/165.01; 604/165.04; 600/585
(58) Field of Search ................................ 606/200, 205, 606/194; 604/523, 524, 526, 528, 164.01, 164.07, 164.12, 164.13, 165.01, 165.02, 165.04, 105, 107, 108, 109

(56) References Cited

U.S. PATENT DOCUMENTS

| | | | |
|---|---|---|---|
| 5,031,636 A | * 7/1991 | Gambale et al. ............ | 600/585 |
| 5,117,838 A | 6/1992 | Palmer et al. .............. | 128/772 |
| 5,133,364 A | 7/1992 | Palermo et al. ............ | 128/772 |
| 5,154,705 A | * 10/1992 | Fleischhacker et al. ..... | 600/585 |
| 5,211,183 A | 5/1993 | Wilson ........................ | 128/772 |
| 5,228,453 A | 7/1993 | Sepetka ...................... | 128/772 |
| 5,234,437 A | 8/1993 | Sepetka ...................... | 606/108 |
| 5,267,573 A | 12/1993 | Evans et al. ................ | 128/772 |
| 5,271,415 A | 12/1993 | Foerster et al. ............. | 128/772 |
| 5,275,173 A | 1/1994 | Samson et al. ............. | 128/772 |
| 5,325,868 A | 7/1994 | Kimmelstiel ............... | 128/772 |
| 5,339,833 A | 8/1994 | Berthiaume ................ | 128/772 |
| 5,365,944 A | 11/1994 | Gambale ..................... | 128/772 |
| 5,373,856 A | 12/1994 | Grenouillet ................ | 128/772 |
| 5,415,178 A | 5/1995 | Hsi et al. .................... | 128/772 |
| 5,421,348 A | 6/1995 | Larnard ...................... | 128/772 |
| 5,776,080 A | * 7/1998 | Thome et al. .............. | 600/585 |
| 5,788,653 A | 8/1998 | Lorenzo ..................... | 600/585 |
| 5,814,062 A | * 9/1998 | Sepetka et al. ............. | 606/198 |
| 5,820,571 A | * 10/1998 | Erades et al. ............... | 600/585 |
| 6,235,001 B1 | * 5/2001 | O'Holloran et al. ... | 604/164.07 |
| 6,248,082 B1 | * 6/2001 | Jafari ......................... | 600/585 |

OTHER PUBLICATIONS

Product Information on CINCH™, a Cinch steerable guidewire extension, 4 pages, from the Cordis® Corporation, 1991.

* cited by examiner

*Primary Examiner*—Michael J. Milano
*Assistant Examiner*—Jessica R Baxter
(74) *Attorney, Agent, or Firm*—David P. Gordon; David S. Jacobson; Thomas A. Gallagher

(57) ABSTRACT

A medical instrument includes a shaft having an outer surface defining an outer diameter, a tube having an inner surface defining an inner diameter and extending over a portion of the shaft, at least one coil wound in a first rotational direction and provided between the shaft and the tube, the at least one coil having a first portion defining an inner surface interfering with an outer surface of the shaft such that the at least one coil grips the shaft, and a second portion coupled to the inner surface of the tube. The tube is movable longitudinally relative to the shaft in a first longitudinal direction when subject to force in the first longitudinal direction, and the tube is substantially immovable longitudinally relative to the shaft in a second longitudinal direction opposite the first longitudinal direction when subject to force in the second longitudinal direction only. When the tube is subject to rotational force in a second rotational direction opposite the first rotational direction, movement of the tube in the second longitudinal direction relative to the shaft is permitted. Other embodiments are also provided.

51 Claims, 5 Drawing Sheets

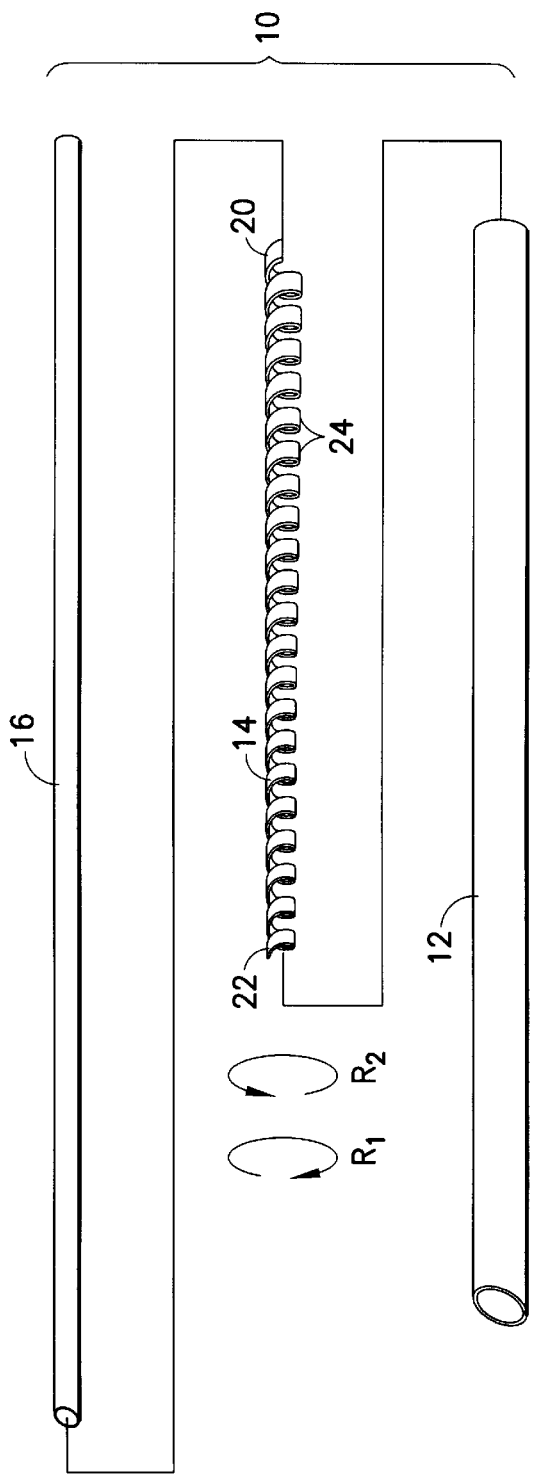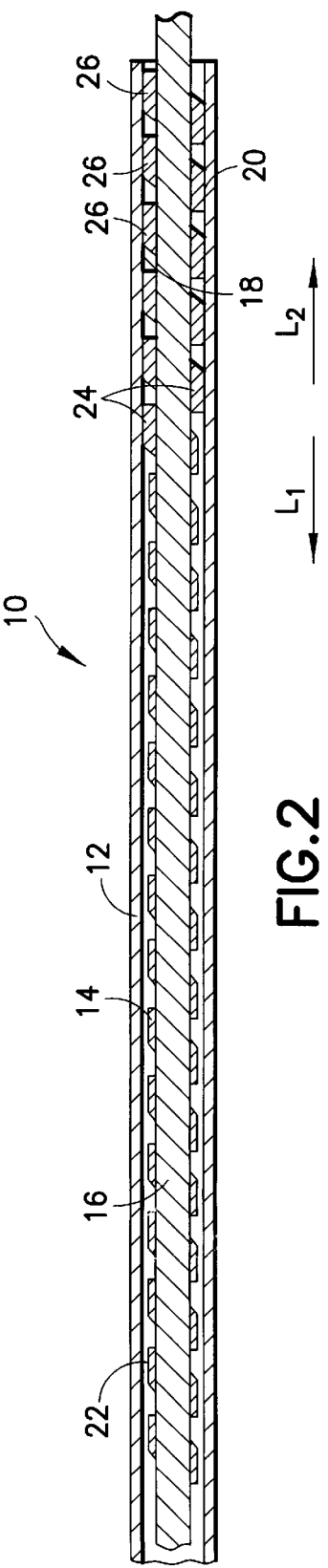
FIG.1
FIG.2

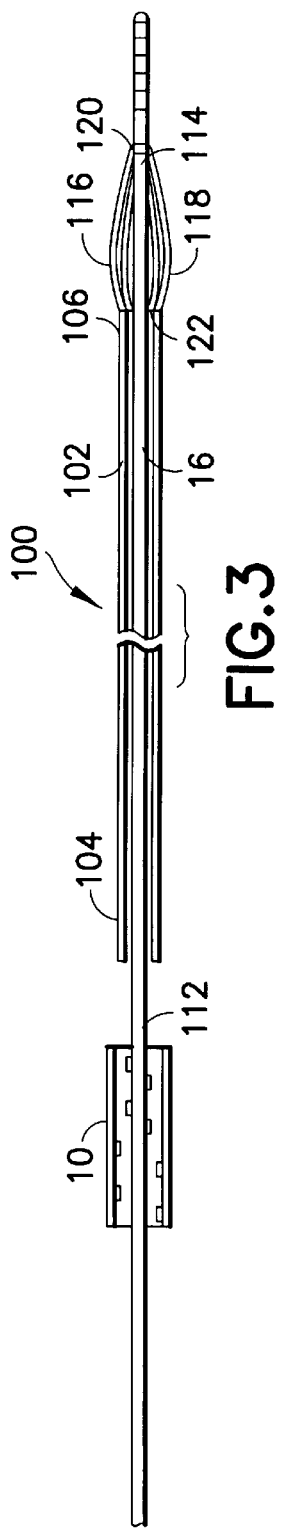
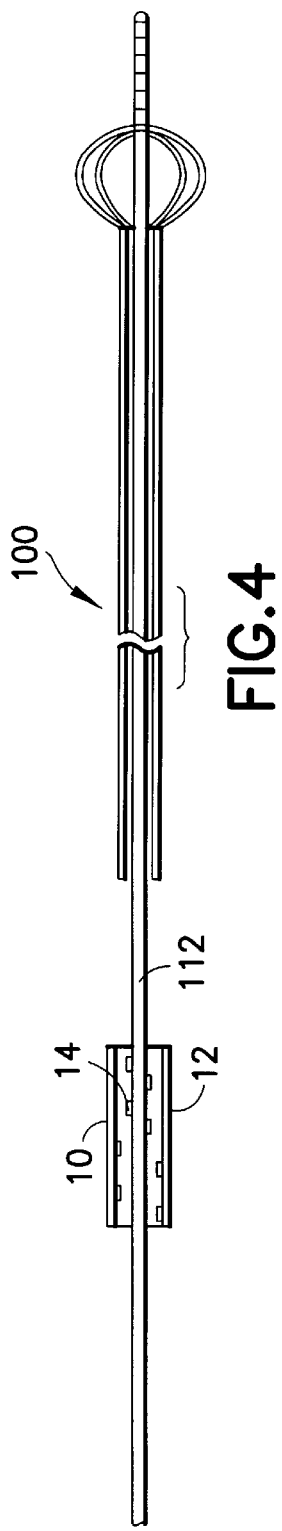
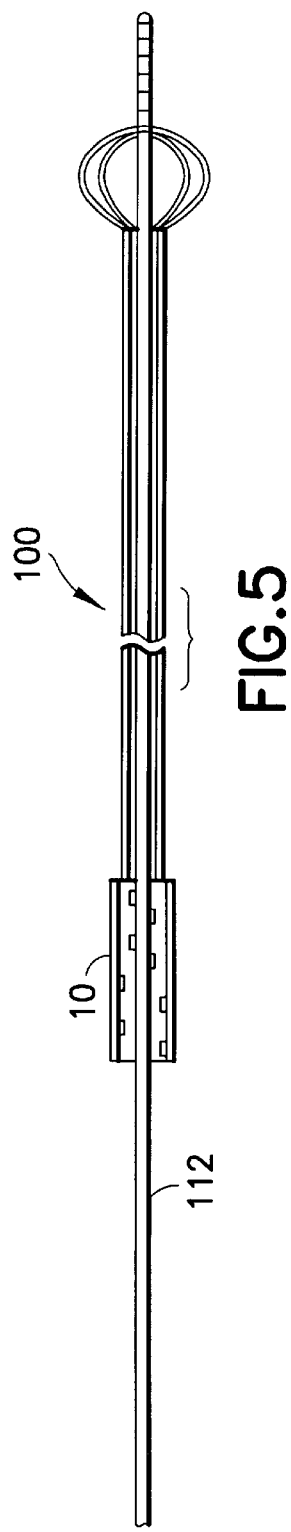

CATCH, STOP AND MARKER ASSEMBLY FOR A MEDICAL INSTRUMENT AND MEDICAL INSTRUMENT INCORPORATING THE SAME

BACKGROUND OF THE INVENTION

1. Field of the Invention

This invention relates broadly to medical instruments. More particularly, this invention relates to a releasable catch, stop, and marker assembly for medical instruments.

2. State of the Art

A variety of medical instruments utilize a configuration in which a shaft member is moved relative to and within a tube. For example, in an endoscopic or intravascular basket device, a shaft having a basket at a distal end thereof is moved within a tube to cause the basket to move between open and closed positions. The relative position of the shaft and the tube is adjusted or maintained by the physician operating the instrument. Yet, the shaft and tube may nevertheless be inadvertently moved relative to each other due to physician error or fatigue. In such instruments it is desirable to be able to automatically maintain the relative positions of the shaft and the tube without relying on the physician. It is also desirable for the relative positions of the shaft and the tube to be easily adjustable.

In other instruments, such as biopsy needle and Veress needles for injection into, e.g., the breast, the liver or the brain, it is desirable to use a stop which sets a maximum depth for the needle such that the needle can be safely inserted to a particular depth and no further. Likewise, it is desirable that a stop be easily adjustable such that the needle is permitted less penetration depth, but be adapted to prevent inadvertent movement in a direction which could cause too much penetration.

On yet other medical devices, for example, a guidewire, it is desirable to have an adjustable marker which indicates a reference depth. As such, the relative position of the tip of the device during a procedure can be determined.

SUMMARY OF THE INVENTION

It is therefore an object of the invention to provide an assembly which can function as a releasable catch, an adjustable stop, or an adjustable marker on a medical device.

It is another object of the invention to provide an assembly which is easily adjustable.

It is a further object of the invention to provide an assembly which is not prone to failure.

It is an additional object of the invention to provide a mechanism which is easy and inexpensive to manufacture.

In accord with these objects, which will be discussed in detail below, an assembly which functions as a catch, stop, or marker, depending on the device on which it is used, is provided. According to a first embodiment of the invention, the assembly includes a tube having an inner surface, a helically wound coil within the tube, and a shaft extending through the coil and which is lockable in longitudinal position relative to the tube. The shaft may be a portion of a shaft of an endoscopic or intravascular instrument, hypodermic tubing of a needle device, a guidewire, etc. The coil has an outer surface coupled to the tube, and an inner surface interfering with the an outer surface of the shaft such that the coil grips the shaft.

In use, the shaft and tube may be slid relative to each other in a first longitudinal direction, but are substantially prevented from sliding relative to each other in an opposite second longitudinal direction. When it is desired to move the tube relative to the shaft in the second longitudinal direction, the tube is rotated relative to the shaft in a first rotational direction (opposite the direction of the winding of the coil) which causes partial unwinding of the coil to at least reduce the interference between the coil and shaft. As such, rotation of the tube in the first rotational direction in combination with longitudinal movement in the second longitudinal direction moves the tube and coil relative to the shaft. Releasing the rotational force on the tube allows the coil to wind back about the shaft and grip and lock the shaft. Rotation of the tube relative to the shaft in the direction of the winding of the coil causes the coil to grip the shaft tighter and substantially prevents any longitudinal movement of the tube and coil relative to the shaft.

According to a second embodiment of the invention, the assembly includes a tube which is rolled partially closed at a first end, and a sleeve within the tube and having an outer diameter substantially the same size or slightly smaller in size than an inner diameter of the tube. The rolling at the first end of the tube operates to retain the sleeve within the first end of the tube. First and second open pitch helically wound coils in a double-helix arrangement are each attached at one end to the sleeve. A shaft extends through the first and second coils, the sleeve, and the tube. The first coil has a first outer surface which interferes with the inner diameter of the tube. The second coil is more tightly wound than the first coil and has an inner surface which interferes with the outer surface of the shaft such that the second coil grips the shaft.

In use, the tube may be slid relative to the shaft in the first longitudinal direction (the direction in which the first and second coils are axially compressible), but is substantially prevented from being slid along the shaft in an opposite second longitudinal direction. Rotation of the tube relative to the shaft in a first rotational direction opposite the direction of the winding of the coils causes partial unwinding of the coils, and the first coil further interfering with the inner surface of the tube. As such, rotation in the direction opposite the coil winding in combination with longitudinal force on the tube relative to the shaft permits the tube and coil to be moved longitudinally along the shaft. Releasing the rotational force on the tube allows the second coil to wind back about the shaft and grip the shaft at a new location. Rotation of the tube relative to the shaft in the direction of the winding of the coils causes the second coil to grip the shaft tighter and prevents any longitudinal movement of the tube and coil relative to the shaft, and also causes the first coil to decrease in diameter such that the first coil and the sleeve rotatably slip within the tube. As such, the second embodiment of the assembly eliminates the potential present in the first embodiment for fixation failure at the coupling of the coil to the tube when the tube is forcibly rotated in the second rotational direction relative to the shaft. In the second embodiment, such force simply causes slippage of the sleeve relative to the tube.

According to a third embodiment, the assembly includes a tube having an inner surface, a generally uniform diameter helically wound coil within the tube, and a shaft extending through the coil. A portion of the coil is attached to the shaft such that the coil and shaft are coupled together.

In use, forcing the tube relative to the shaft in a first longitudinal direction axially compresses the coil and results in an increased diameter of the coil which substantially prevents the shaft and coil from movement with the tube. Forcing the tube relative to the shaft in an opposite second longitudinal direction operates to axially extend the coil within the tube such that its diameter is reduced and movement of the shaft and coil relative to the tube is facilitated. When it is desired to move the tube relative to the shaft in the first longitudinal direction, the tube is rotated relative to the shaft in the direction of the winding of the coil, which causes radial compression of the coil thereby permitting the coil and shaft to slide within the tube.

It will be appreciated that where the shaft is a portion of the shaft of a medical instrument, e.g. a laparoscopic, endoscopic, or intravascular instrument, the embodiments of the assembly of the invention permit locking the shaft in a position relative to a tube through which the shaft extends. In addition, the shaft may be a medical instrument requiring an easily and quickly adjustable stop along a length of a shaft, e.g., a needle. As such, the assembly may be positioned along a length of the needle to prevent penetration beyond the stop. Adjustment of the stop in a 'safe' direction (e.g., in a direction which would further limit penetration of the needle into the human body) can be made by simply sliding the stop along the shaft. Adjustment in a 'stopped' direction (e.g., in a direction which would permit greater needle penetration) is possible by applying rotational force to the tube relative to the shaft such that the coil about the shaft is partially unwound, moving the tube along the shaft, and then releasing the rotational force to engage the tube about the shaft. Likewise, the assembly can be used as an adjustable marker on a guidewire or similar device to indicate the length of the portion of the guidewire is inserted into a body.

Additional objects and advantages of the invention will become apparent to those skilled in the art upon reference to the detailed description taken in conjunction with the provided figures.

BRIEF DESCRIPTION OF THE DRAWINGS

FIG. 1 is an exploded view of an assembly which functions as a catch, stop, and marker according to a first embodiment of the invention;

FIG. 2 is a longitudinal section of the assembly according to the first embodiment of the invention;

FIG. 3 through 5 illustrate the assembly according to the first embodiment of the invention utilized as a catch on an endoscopic or intravascular instrument;

DETAILED DESCRIPTION OF THE PREFERRED EMBODIMENTS

Figure 6:
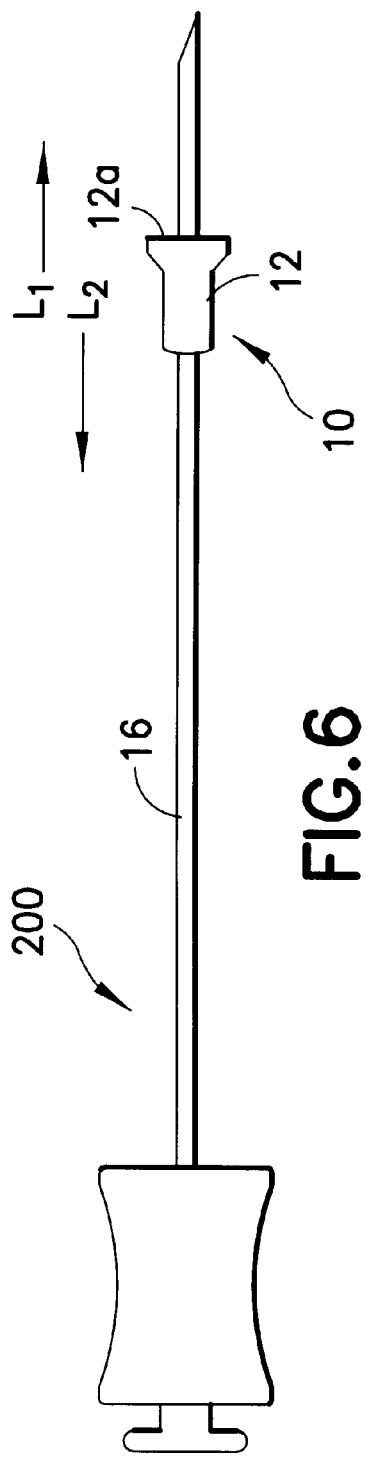
FIG. 6 illustrates the assembly according to the first embodiment of the invention utilized as an adjustable stop on a needle device.

Turning now to FIGS. 1 and 2, an assembly 10 which functions as a catch, stop, or marker, depending on the device on which it is used, is provided. According to a first embodiment of the invention, the assembly 10 includes a tube 12, an open pitch helically wound flat wire coil 14 within the tube, and a shaft 16 extending through the coil. As discussed in more detail and with examples below, the shaft 16 may be a portion of a shaft of an endoscopic or laparoscopic instrument, the hollow and substantially rigid hypodermic tubing of a needle device, a flexible guidewire, etc.

The tube 12 has an inner surface 18 defining an inner diameter. The coil has first and second ends 20, 22, and a transition section 24 between two coil diameters. The first end 20 of the coil 14 has an outer diameter slightly larger than the inner diameter of the tube 12, e.g., with an interference of approximately 0.0005 inch–0.002 inch, and an inner diameter greater than the outer diameter of the shaft 16. The first end 20 is bonded, e.g., by gluing, soldering, brazing, or most preferably laser welding, at 26 to the inner surface 18 of the tube. The interference ensures coil contact with the inner surface 18 of the tube to facilitate the bond 26. The second end 22 of the coil 14 has an outer diameter smaller than the inner diameter of the tube 12 and an inner diameter slightly smaller than the outer diameter of the shaft 16 such that the second end 22 of the coil 14 grips the shaft 16. This slight interference ensures that the coil 14 sufficiently grips the shaft 16. Typical values of coil/shaft interference are 0.001 inch–0.0005 inch on the diameter.

Referring to FIG. 2, in use, forcing the tube 12 relative to the shaft 16 in a first longitudinal direction $L_1$ (the direction from the first end 20 with the larger outer diameter toward the second end 22 with the smaller inner diameter) axially compresses the coil 14 and results in an increased diameter for the second end 22 of the coil. The tube 12 may then be slidably moved relative to the shaft 16. However, the tube and shaft are prevented from sliding relative to each other in an opposite second longitudinal direction $L_2$, as force only in the second longitudinal direction $L_2$ operates to contract the second end 22 of the coil 14 about the shaft 16. When it is desired to move the tube 12 relative to the shaft 16 in the second longitudinal direction $L_2$, the tube 12 is rotated relative to the shaft 16 in a first rotational direction $R_1$ (opposite the direction of the winding of the coil). Rotation in the first rotational direction $R_1$ causes partial unwinding of the coil 14 which results in the second end of the coil assuming a relatively larger diameter; i.e., larger than the outer diameter of the shaft. As such, rotation of the tube 12 in the first rotational direction $R_1$ in combination with longitudinal force on the tube permits movement of the tube and coil relative to the shaft. Releasing the rotational force on the shaft allows the coil to wind back about the shaft and grip the shaft in the new position relative to the tube. Rotation of the tube relative to the shaft in a second rotational direction $R_2$ (in the direction of the winding of the coil) causes the coil to grip the shaft tighter and prevents any longitudinal movement of the tube and coil relative to the shaft.

The operation of the assembly is affected by the materials used and the sizes of the components. While no particular size is required for the tube, and there is no upper limit on the dimensions, two tubes which have been used successfully include one with an outer diameter 0.032 inch and an inner diameter of 0.023 inch, and another with an outer diameter of 0.014 inch and an inner diameter of 0.010 inch, such that the tube (and the entire catch) is sized to permit small catheters such as balloon catheters thereover. These tubes were approximately 1.2 inches in length, and are limited in minimum length only by the length of the coil required to grip the wire. In addition, the tube is preferably given a size which facilitates gripping with human fingers. The tube may be made from standard gauge hypodermic tubing (304 stainless steel), other stainless steels (316, 17-4, etc.), Nitinol, brass, or other suitable materials.

The coil 14 is preferably made from a high tensile material, such as 304 stainless steel. Exemplar thicknesses for the material of the flat wound coils is preferably in the range of 0.0008 inch to 0.003 inch, though other thicknesses can be used. the pitch of the coil is calculated based on the extent to which the inner diameter of the coil increases when the coil is fully compressed, and provides an indication of ease with which the shaft will slide through the coil when the catch, stop or marker is advanced. Exemplar pitches of the coils are preferably 0.015 inch to 0.026 inch, though other pitches can be used. In addition, hysteresis can be controlled; that is, the distance the catch/stop retracts when slid into a position in the $L_1$ direction. Hysteresis is a result of at least two factors: slight residual compression of the coil during advancement which relaxes when the advancement stops, and unconstrained winds of coil where the coil transitions at 24 (FIG. 1). The transition 24 from the open first end 20 of the coil 14 to the gripping second end 22 is preferably an immediate transition where it is desired to minimize hysteresis and a more gradual transition where it is desired to increase hysteresis. In addition, as the longitudinal stiffness of the coil is increased, the residual compression of the coil during advancement is decreased, thus further minimizing hysteresis. In addition, the direction of the pitch (right or left hand) of the coil determines the direction in which the tube must be rotated relative to the shaft in order to defeat the grip of the coil. Therefore, depending upon the application, the pitch can be set to either right or left hand.

The diameter of the shaft has no maximum, but as stated above must be relatively smaller than the inner diameter of the first end of the coil. Successfully used shaft diameters range from 0.008 inch to 0.014 inch. The shaft is preferably made from 304 stainless steel, and preferably has a substantially smooth surface.

In order to more clearly describe the function of the catch-stop assembly 10 of the invention, the use of the assembly will now be described with respect to several exemplar medical instruments. Turning now to FIGS. 3 through 5, the use of the assembly 10 is shown with respect to an endoscopic or intravascular instrument, and particularly a basket device 100. Referring to FIG. 3, the basket device 100 includes a tubular member 102 having a proximal end 104 and a distal end 106, a shaft 16 extending through the tubular member 102 and having a proximal end 112 and a distal end 114, and a basket 116 at the distal ends 106, 114 of the tubular member and shaft. More particularly, the basket 116 includes a plurality of strands 118 each having one end 120 coupled to the distal end 114 of the shaft 16 and another end 122 coupled to the distal end 106 of the tubular member 102. The strands 118 are biased to extend longitudinally such that in a relaxed state they are held substantially against the shaft 16; i.e., with the basket 116 in a closed position. Referring to FIG. 4, movement of the shaft 16 proximally relative to the tubular member 102 causes the strands 118 to bow outward and the basket 116 to assume an expanded configuration. At a proximal portion of the shaft 16, the assembly 10 is provided. The first end 20 of the coil 14 grips the shaft 16. Referring to FIG. 5, the assembly 10 may be slid distally along the shaft 16 (in the $L_1$ direction, FIG. 2) to abut against the proximal end 104 of the tubular member 102. The assembly is locked from sliding proximally (in the $L_2$ direction, FIG. 2), and thus temporarily secures the basket 116 in the expanded configuration, against the bias of the strands 118. Then, when it is desired to collapse the basket 116, the tube 12 is rotated in a direction opposite the winding of the coil 14 (in the $R_1$ direction, FIG. 1) such that the coil 14 releases its grip on the shaft 16, and the assembly can be slid proximally along the shaft 16 (back to the position shown in FIG. 4), permitting the basket to collapse (as shown in FIG. 3). If desired, a collet or other device can be used to couple the distal or proximal end of the basket to the shaft or the tube so that when the tube is rotated, the basket strands do not twist.

Likewise, the assembly 10 may be used on a basket device in which the strands of the basket are coupled solely to the shaft, and not the tubular member, and in which the strands are biased to bow outward from the shaft to naturally take an expanded configuration. The assembly 10 can lock the shaft relative to the tubular member such that the basket is maintained in an expanded configuration, preferably adjacent the distal end of the tubular member, or in a collapsed configuration in which the basket is withdrawn into the distal end of the tubular member. In any such instrument, the device can be made of such small size that it permits other instruments, such as catheters, from being extended thereover.

Turning now to FIG. 6, the assembly 10 may also be used as a stop on a needle device 200, e.g., a biopsy needle or a Veress needle. The needle device 200 has a needle 16 for introduction or removal of fluid, which functions as the shaft 16. The assembly 10 is positioned along a length of the needle 16 and limits penetration beyond the assembly 10. The tube 16 of the assembly can be provided with a relatively large distal end 12a to facilitate its function as a stop against a portion of the human body. Adjustment of the stop assembly 10 along the needle 16 in a 'safe' $L_1$ direction (i.e., in a direction which would further limit penetration of the needle into the human body) can be made by simply sliding the stop along the shaft. Adjustment in an opposite $L_2$ direction (e.g., in a direction which would permit greater needle penetration) is possible by applying rotational force to the tube 12 relative to the needle 16 such that the coil gripping the needle is partially unwound. The tube is then repositioned along the needle, and the rotational force on the tube is released such that the coil again engages the tube about the shaft.

Figure 7:
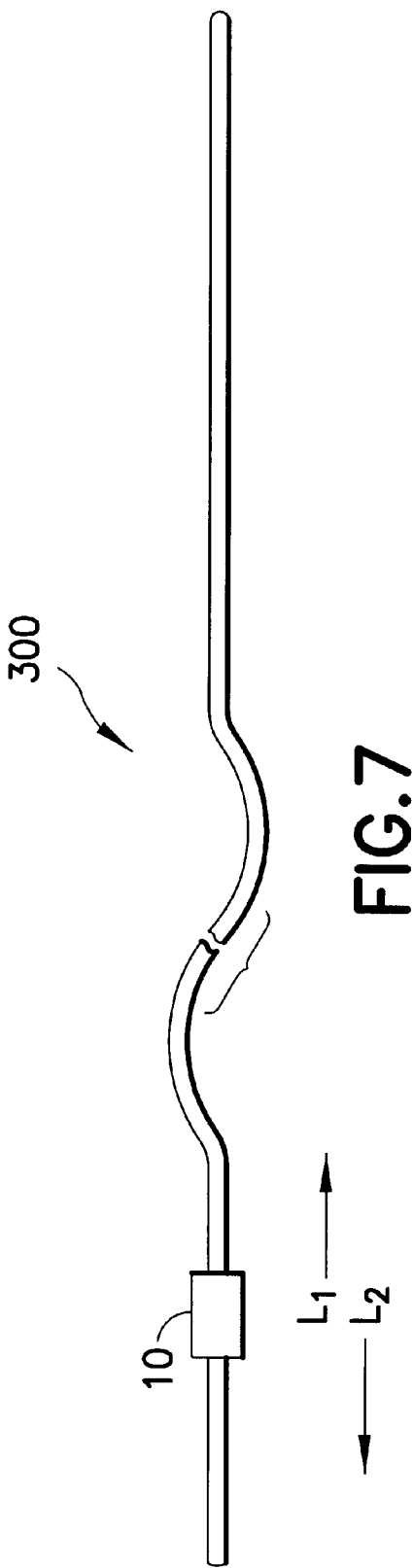
FIG. 7 illustrates the assembly according to the first embodiment of the invention utilized as a reference marker on a guidewire.

Referring now to FIG. 7, the assembly 10 can be utilized as an adjustable marker on a guidewire 300 to indicate the length of the portion of the guidewire which is inserted into a body. The guidewire functions as the shaft 16 of the assembly 10. The assembly 10 can be easily positioned at a location on the length of the guidewire, and its position is maintained. As such, a position which represents a particular amount, e.g., 60 cm, of penetration of the guidewire into the body. The position is marked until the assembly is forcibly slid in a 'safe' $L_1$ direction (thereby permitting less guidewire penetration into the body), or rotated and slid in an opposite $L_2$ direction (thereby permitting greater penetration).

Figure 8:
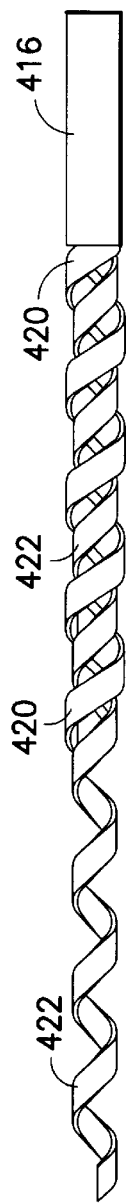
FIG. 8 is a side elevation of a double coil and sleeve subassembly of an assembly according to a second embodiment of the invention.
Figure 9:
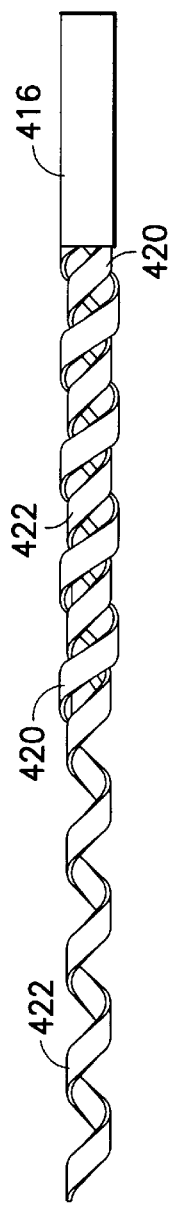
FIG. 9 is a side elevation of the double coil and sleeve subassembly of the assembly according to the second embodiment of the invention, shown axially rotated 180° relative to FIG. 8.
Figure 10:
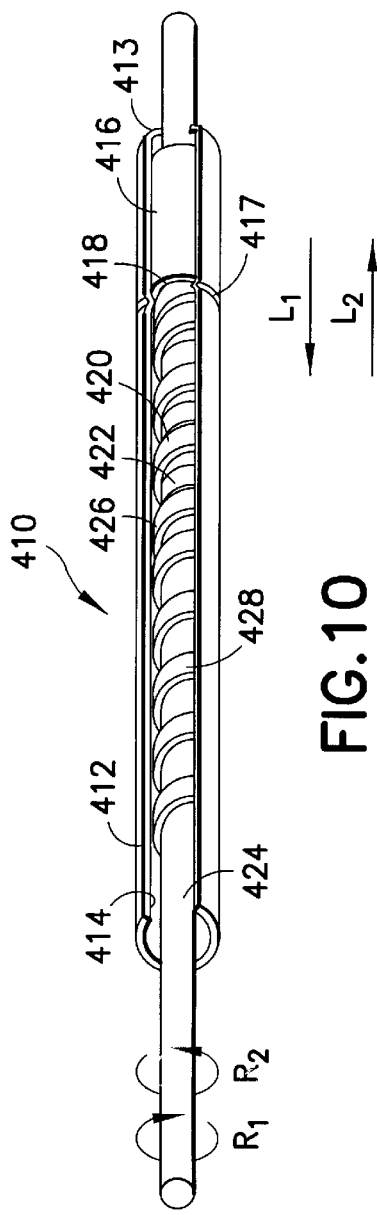
FIG. 10 is a partial section of the assembly according to the second embodiment of the invention.

Turning now to FIGS. 8 through 10, a second embodiment of the assembly 410 of the invention is shown. The assembly 410 includes a tube 412 having an inner surface 414 defining an inner diameter and being rolled partially closed at a first end 413, and a sleeve 416 within the tube 412 and having an outer diameter substantially the same size or slightly smaller in size than the inner diameter of the tube. The rolling at the first end 413 of the tube 412 operates to retain the sleeve 416 within the first end 413 of the tube. In addition, optionally, a groove 417 may be rolled into or otherwise formed in the tube to provide an internal annular protrusion 418 which operates to maintain the longitudinal position of the sleeve within the tube 412 while permitting the sleeve to rotate relative to the tube; i.e., forming a swivel joint between the sleeve and the tube. First and second open pitch helically wound flat wire coils 420, 422 in a double-helix arrangement are attached at one end within the sleeve 416. A shaft 424 extends through the first and second coils 420, 422, the sleeve 416, and the partially closed end 413 of the tube 412.

The first coil 420 has a first outer diameter which is slightly larger than the inner diameter of the tube 412, such that the outer surface 426 of the first coil 420 contacts the inner surface 414 of the tube. The inner diameter of the first coil 420 is larger than the outer diameter of the shaft 424 such that the first coil 420 and the shaft 424 are not in contact. The second coil 422 is more tightly wound than the first coil 420 and has an inner diameter slightly smaller than the outer diameter of the shaft 424 such that the second coil grips the shaft. The outer diameter of the second coil 422 is smaller than the inner diameter of the tube 412 such that the outer surface 428 of the second coil and the inner surface 414 of the tube are not in contact. The inner and outer diameters of the first and second coils 420, 422 are preferably substantially uniform along their respective lengths.

In use, the tube 412 may be slid relative to the shaft 424 in a first longitudinal direction $L_1$ (such that the rolled first end 413 provides force against the sleeve 416 and operates to axially compress the second coil 422 and release the shaft 424 from the grip of the second coil 422), but cannot be slid in an opposite second longitudinal direction $L_2$. Rotation of the tube 412 relative to the shaft 424 in a first rotational direction $R_1$ (opposite the direction of the winding of the coils 420, 422) causes partial unwinding of the coils 420, 422 which results in the inner diameter of the second coil 422 assuming a size larger than the outer diameter of the shaft 424, and the first coil 420 increasing its contact against the inner surface 414 of the tube 412. As such, relative rotation of the tube 412 and shaft 424 in the first rotational direction $R_1$ in combination with longitudinal force on the tube permits the tube and coils to be moved along the shaft. Releasing the rotational force on the tube 412 allows the second coil 422 to wind back about the shaft 424 and grip the shaft in the new position. Rotation of the tube relative to the shaft in a second rotational direction $R_2$ (in the direction of the winding of the coils) causes the second coil 422 to grip the shaft tighter and substantially prevents any longitudinal movement of the shaft relative to the tube and coils. In addition, rotation in direction $R_2$ causes the first coil 420 to decrease in diameter such that the first coil and the sleeve 416 rotatably slip within the tube 412.

As such, the second embodiment of the assembly eliminates the potential present in the first embodiment for fixation failure at the bond 26 between the coil 14 and the tube 12 when the tube 12 is forcibly rotated in the second rotational direction $R_2$ relative to the shaft 16 (FIG. 2). In the third embodiment, such force simply causes slippage of the sleeve 416 relative to the tube 414 (FIG. 10).

Figure 11:
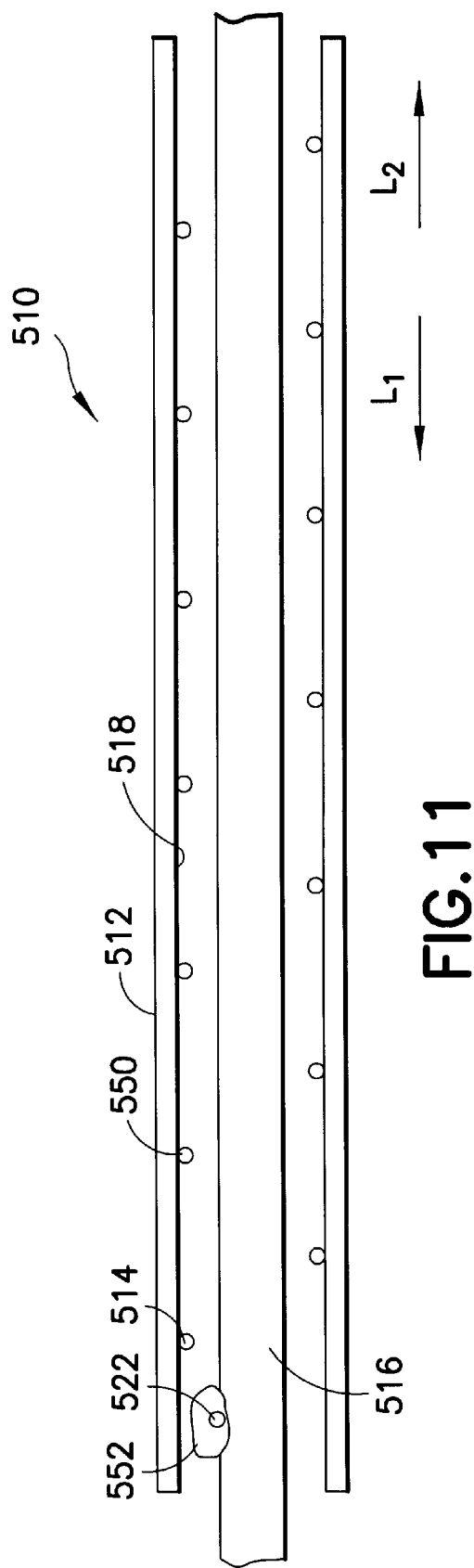
FIG. 11 is a side elevation of a third embodiment of an assembly according to a second embodiment of the invention.

Referring now to FIG. 11, a third embodiment of the assembly of the invention substantially similar to the first embodiment (with like parts having numbers incremented by 500) is shown. The assembly 510 includes a tube 512 having an inner surface 518 defining an inner diameter, a preferably open pitch, helically wound, flat wire coil 514, and a shaft 516 extending through the coil and tube. The coil 514 has a first outer diameter which is equal to or slightly larger than the inner diameter of the tube 512, such that the outer surface 550 of the coil 514 interferes with the inner surface 518 of the tube. The inner diameter of the coil 514 is larger than the outer diameter of the shaft 516 such that the coil and the shaft are not generally in contact and the coil, except at one end 522, e.g., a proximal end, is generally uniform in inner and outer diameters. The end 522 of the coil 514 is attached to the shaft 516, e.g., by a weld 552.

In use, forcing the tube 512 relative to the shaft 516 in a first longitudinal direction $L_1$ axially compresses the coil 514 and results in an increased diameter of the coil which substantially prevents the shaft 516 and coil 514 from movement with the tube 512. Forcing the tube 512 relative to the shaft 516 in an opposite second longitudinal direction $L_2$ operates to axially extend the coil 514 within the tube 512 such that its diameter is reduced and movement of the shaft 516 and coil 514 relative to the tube 512 is facilitated. When it is desired to move the tube 512 relative to the shaft 516 in the first longitudinal direction $L_1$, the tube 512 is rotated relative to the shaft 516 in a first rotational direction $R_1$ (in the direction of the winding of the coil) which causes winding of the coil 514 and results in the coil assuming a smaller diameter thereby permitting the coil and shaft to slide within the tube.

The second and third embodiments of the assembly 410, 510 may be used in the same applications as the first embodiment.

While it is preferable that the coil or coils in the embodiments be open wound, i.e., have gaps between the adjacent windings, the coils may be close wound with substantially no gaps between adjacent windings. Where a coil is close wound, the coil is unable to compress and increase its outer diameter as the shaft is pushed therethrough to allow the shaft to move relative to the coil. Therefore, a different mechanism must be provided which permits the shaft to move relative to the coil. For example, the close wound coil may be provided with an inner diameter approximately equal to or slightly larger than the outer diameter of the shaft. Such a coil is provided with some or all of its windings deformed such that they are have an effective diameter which is decreased to interfere with the outer diameter of the shaft. The deformation can be accomplished in many ways. By way of example, and not by limitation, (1) the end winding or several individual windings may be bent inward, (2) a portion of the entirety of the coil may be flattened, (3) inward indentations may be formed in the wire of the coil, (4) the coil may be bent so that it is wavy, (5) etc. Then, when the shaft is pushed through the coil in a direction of coil "compression", the shaft interferes with the windings of the coil that are deformed, yet remains capable of being forced therethrough. However, when the shaft is pulled in a direction that tends to elongate the coil, the deformed windings frictionally engage the coil and the coil becomes more elongate, tightening its grip. The shaft is released by rotating the assembly such that the inner diameter of the coil is effectively increased and simultaneously sliding the coil relative to the shaft.

There have been described and illustrated herein several embodiments of an assembly usable as a catch, stop, and/or marker on a medical instrument. While particular embodiments of the invention have been described, it is not intended that the invention be limited thereto, as it is intended that the invention be as broad in scope as the art will allow and that the specification be read likewise. Thus, while the use of the assembly has been shown on several exemplar medical instruments, the examples are not limitations on the application of the invention, as the invention may be used with myriad other medical devices to provide a catch, a stop, or a marker. For example, the invention may also be used as a catch on a snare device. In addition, the shaft may be either a solid or tubular element, and of a flexible or rigid construction. Moreover, while a needle device has been stated as having a substantially rigid needle, the needle tubing may also be a flexible catheter. Also, while the coil element has been described as being flat, the coil element may alternatively have another cross-sectional shape, e.g., round, oval or rectangular, along a portion or its entirety. In addition, while the tube, coil, and shaft have been shown as being cylindrical in shape, it will be appreciated that each may have another cross-sectional shape, e.g., rectangular or hexagonal. Further, while the inner dimension of the coil is stated as being smaller than the outer dimension of the shaft, it may be equal in size or even larger, provided that an interference (via shape, friction, or other coupling) is obtained between the two. Likewise, the outer dimension of the coil is stated as being preferably larger than the inner dimension of the tube, yet it may be equal in size or smaller, provided that a coupling (via shape, friction, bonding, or other coupling) is obtained between the two. Moreover, while it is preferred that the coil in the first embodiment and coils in the second embodiment define two inner and two outer dimensions, the coil may have uniform inner and outer dimensions along its length. Also, while in the first embodiment the coil has been described as being bonded to the tube, it will be appreciated that a ratchet mechanism may be utilized which prevents rotation in the $R_1$ direction but permits rotation in the $R_2$ direction, thereby eliminating any concerns regarding the failure of the bond. In addition, while the second embodiment has been described with respect to a particular swivel joint, it will be appreciated that other swivel joints may be used. Furthermore, while particular materials and dimensions have been provided, it will be understood that other materials and components of other sizes can be similarly used. It will therefore be appreciated by those skilled in the art that yet other modifications could be made to the provided invention without deviating from its spirit and scope as claimed.

What is claimed is:

1. A medical instrument, comprising:
   a) a shaft having an outer surface;
   b) a tubular element having an inner surface extending over a portion of said shaft; and
   c) at least one coil wound in a first rotational direction and provided between said shaft and said tubular element, said at least one coil having an inner surface and an outer surface, said inner surface of said at least one coil interfering with said shaft such that said at least one coil grips said shaft, and said outer surface of said coil coupled to said tubular element,
   wherein said tubular element is movable longitudinally relative to said shaft in a first longitudinal direction when subject to force in said first longitudinal direction, and said tubular element is substantially immovable longitudinally relative to said shaft in a second longitudinal direction opposite said first longitudinal direction when subject to force in said second longitudinal direction only, and
   wherein when said tubular element is subject to rotational force in a second rotational direction opposite said first rotational direction, movement of said tubular element in said second longitudinal direction relative to said shaft is permitted, and
   further wherein when said rotational force in said second rotational direction is released said tubular element is substantially immovable relative to said shaft in said second longitudinal direction.

2. A medical instrument according to claim 1, wherein: said at least one coil is at least one flat wound coil.

3. A medical instrument according to claim 1, wherein: said at least one coil is an open pitch coil.

4. A medical instrument according to claim 1, wherein: said shaft and said tubular element each have substantially circular cross-sectional shapes.

5. A medical instrument according to claim 1, wherein: said outer surface of said shaft defines an outer dimension, and said inner surface of said at least one coil has an inner diameter at least as small as said outer dimension of said shaft,
said inner surface of said tubular member defines an inner dimension, and said outer surface of said at least one coil defines an outer diameter at least as large as said inner dimension of said tubular member.

6. A medical instrument according to claim 1, wherein: said at least one coil has a first portion defining a first inner diameter and a first outer diameter and a second portion having a second inner diameter greater than said first inner diameter and a second outer diameter greater than said first outer diameter.

7. A medical instrument according to claim 6, wherein: said inner surface of said tubular element defines an inner diameter, and said second outer diameter of said at least one coil is larger than said inner diameter of said tubular element.

8. A medical instrument according to claim 1, wherein: said second portion of said at least one coil is bonded to said inner surface of said tubular element.

9. A medical instrument according to claim 1, wherein: said force in said first longitudinal direction compresses said at least one coil.

10. A medical instrument according to claim 1, wherein: said at least one coil is a single coil.

11. A medical instrument according to claim 1, wherein: said at least one coil comprises first and second coils arranged in a double helix arrangement.

12. A medical instrument according to claim 11, wherein: said first and second coils are open wound coils.

13. A medical instrument according to claim 11, wherein: said first coil defines a first inner diameter and a first outer diameter, and said second coil defines a second inner diameter greater than said first inner diameter and a second outer diameter greater than said first outer diameter.

14. A medical instrument according to claim 11, further comprising:
    d) a sleeve, wherein one end of each of said first and second coils is coupled to said sleeve.

15. A medical instrument according to claim 14, wherein: said tubular element is partially closed at one end to retain said sleeve.

16. A medical instrument according to claim 14, wherein: a rotational joint is provided between said sleeve and said tubular element.

17. A medical instrument according to claim 1, wherein: said shaft is flexible.

18. A medical instrument according to claim 1, wherein: said shaft is rigid.

19. A medical instrument according to claim 1, wherein: said shaft is tubular.

20. A medical instrument according to claim 1, wherein: said outer surface of said shaft is substantially smooth.

21. A medical instrument according to claim 1, wherein:
said tubular element is made from one of stainless steel, nickel-titanium and brass.

22. A medical instrument according to claim 1, wherein:
said coil is made from stainless steel.

23. A medical instrument according to claim 1, wherein:
said at least one coil has a thickness approximately in the range of 0.0008 inch to 0.003 inch.

24. A medical instrument according to claim 1, wherein:
said at least one coil has a pitch in the range of approximately 0.015 inch to 0.026 inch.

25. A medical instrument according to claim 1, wherein:
said tubular member has an outer diameter at least as small as 0.032.

26. A medical instrument according to claim 1, wherein:
said shaft is a guidewire.

27. A medical instrument according to claim 1, wherein:
said shaft is a fluid introduction or removal element of a needle device.

28. A medical instrument according to claim 1, wherein:
said shaft is coupled to one of a snare and a basket.

29. An assembly for use with a medical instrument including a shaft having an outer surface, comprising:
 a) a tubular element having an inner surface extending over a portion of the shaft; and
 b) a coil wound in a first rotational direction and provided between the shaft and said tubular element, said coil having an inner surface interfering with the outer surface of the shaft, and an outer surface coupled to said inner surface of said tubular element,
 wherein said tubular element is movable longitudinally relative to the shaft in a first longitudinal direction when subject to force in said first longitudinal direction, and said tubular element is substantially immovable longitudinally relative to the shaft in a second longitudinal direction opposite said first longitudinal direction when subject to force in said second longitudinal direction only, and
 wherein when said tubular element is subject to rotational force in a second rotational direction opposite said first rotational direction, movement of said tubular element in said second longitudinal direction relative to the shaft is permitted, and
 further wherein when said rotational force in said second rotational direction is released said tubular element is substantially immovable relative to the shaft in said second longitudinal direction.

30. An assembly according to claim 29, wherein:
wherein said coil is an open pitch coil.

31. An assembly according to claim 29, wherein:
said coil has a first end having an inner diameter smaller than a dimension of the outer surface of the shaft.

32. An assembly according to claim 29, wherein:
said coil has a first end biased to an inner diameter at least as small as a dimension of the outer surface of the shaft such that said first end of said coil grips the outer surface of the shaft, and said coil has a second end biased to an outer diameter sized such that said second end of said coil contacts said inner surface of said tubular element.

33. An assembly according to claim 32, wherein:
movement in said first longitudinal direction compresses said coil such that said inner diameter of said first end of said coil increases.

34. An assembly according to claim 29, wherein:
said outer surface of said coil is bonded at a bond to said inner surface of said tubular element.

35. An assembly according to claim 34, wherein:
said bond is one of a glue bond, a solder bond, a brazed bond, and a weld.

36. An assembly for use with a medical instrument including a shaft having an outer surface, comprising:
 a) a tubular element having an inner surface extending over a portion of the shaft; and
 b) a first coil wound in a first rotational direction and provided between the shaft and said tubular element, said first coil having an inner surface interfering with the outer surface of the shaft;
 c) a second coil wound in said first rotational direction and provided in a double helix arrangement with said first coil, said second coil having an outer surface coupled to said inner surface of said tubular element; and
 d) a coupling element which couples said first coil to said second coil,
 wherein said tubular element is movable longitudinally relative to the shaft in a first longitudinal direction when subject to force in said first longitudinal direction, and said tubular element is substantially immovable longitudinally relative to the shaft in a second longitudinal direction opposite said first longitudinal direction when subject to force in said second longitudinal direction only, and
 wherein when said tubular element is subject to rotational force in a second rotational direction opposite said first rotational direction, movement of said tubular element in said second longitudinal direction relative to the shaft is permitted, and
 further wherein when said rotational force in said second rotational direction is released said tubular element is substantially immovable relative to the shaft in said second longitudinal direction.

37. An assembly according to claim 36, wherein:
said first and second coils are open pitch coils.

38. An assembly according to claim 36, wherein:
said first coil has an inner diameter biased to a dimension at least as small as the outer surface of the shaft.

39. An assembly according to claim 36, wherein:
said second coil has an outer diameter biased to a dimension at least as large as an inner diameter of said inner surface of said tubular member.

40. An assembly according to claim 36, wherein:
movement in said first longitudinal direction compresses said first coil such that an inner diameter of said first coil increases.

41. An assembly according to claim 36, wherein:
said coupling element is a sleeve.

42. An assembly according to claim 36, wherein:
said first coil has substantially uniform first inner and first outer diameters along its length, and said second coil has substantially uniform second inner and second outer diameters along its length.

43. An assembly according to claim 36, wherein:
said coupling element is coupled in said tubular element at a rotatable joint.

44. An assembly according to claim 36, wherein:
said tubular element has an end which is partially closed but sufficiently open to permit extension of the shaft therethrough.

45. A medical instrument, comprising:
a) a shaft having an outer surface;
b) a tubular element having an inner surface extending over a portion of said shaft; and
c) a coil provided between said shaft and said tubular element, said coil interfering with one of said shaft and said inner surface of said tubular element and said coil being attached to said other of said shaft and said inner surface of said tubular element,
wherein said tubular element is movable longitudinally relative to said shaft in a first longitudinal direction when subject to force in said first longitudinal direction, and said tubular element is substantially immovable longitudinally relative to said shaft in a second longitudinal direction opposite said first longitudinal direction when subject to force in said second longitudinal direction only, and
wherein when said tubular element is subject to rotational force in a first rotational direction, movement of said tubular element in said second longitudinal direction relative to said shaft is permitted, and further wherein when said rotational force in said first rotational direction is released said tubular element is substantially immovable relative to said shaft in said second longitudinal direction.

46. A medical instrument according to claim 45, wherein:
said coil interferes with said inner surface of said tubular element and a portion of said coil is attached to said shaft.

47. A medical instrument according to claim 46, wherein:
said portion at which said coil is attached to said shaft is an end of said coil.

48. A medical instrument according to claim 45, wherein:
said coil wound is wound in said first rotational direction.

49. A medical instrument according to claim 45, wherein:
said coil is a flat wound coil.

50. A medical instrument according to claim 45, wherein:
said coil is an open pitch coil.

51. A medical instrument according to claim 45, wherein:
said shaft is coupled to one of a snare and a basket.

* * * * *